United States Patent

Bathelt

[11] 4,124,469
[45] Nov. 7, 1978

[54] PERFLUOROALKYLACETYL CHLORIDE PROCESS

[75] Inventor: Heinrich Bathelt, Altötting, Fed. Rep. of Germany

[73] Assignee: Hoechst Aktiengesellschaft, Frankfurt am Main, Fed. Rep. of Germany

[21] Appl. No.: 846,709

[22] Filed: Oct. 31, 1977

Related U.S. Application Data

[62] Division of Ser. No. 751,013, Dec. 16, 1976, abandoned.

[30] Foreign Application Priority Data

Dec. 24, 1975 [DE] Fed. Rep. of Germany ....... 2558711
Dec. 24, 1975 [DE] Fed. Rep. of Germany ....... 2558728

[51] Int. Cl.² .............................................. B01J 1/10
[52] U.S. Cl. ................. 204/163 R; 204/161; 260/408
[58] Field of Search ............. 204/161, 163 R; 260/544 L, 408

[56] References Cited

U.S. PATENT DOCUMENTS 3,706,773  12/1972  Anello et al. ............... 260/544 L
4,002,657   1/1977  Jäger ............................... 260/408

OTHER PUBLICATIONS

Francis et al., Chemical Society Journal (London), 1955, pp. 2151 to 2163.

*Primary Examiner*—Leland A. Sebastian
*Attorney, Agent, or Firm*—Connolly and Hutz

[57] ABSTRACT

Perfluoroalkylacetyl chlorides of the formula

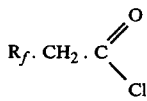

I.

wherein $R_f$ represents a straight-chain perfluoroalkyl radical having from 4 to 12 carbon atoms which are prepared by reacting perfluoro alkyl ethanols having general formula

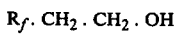

II.

wherein $R_f$ has the same meaning as in formula I, with chlorine under exposure to UV irradiation, in the presence of an inert organic solvent, at temperatures of from −20° C to +120° C. These acetyl chlorides are intermediates for the preparation of the corresponding esters with polyglycols which serve as dry cleaning detergents.

1 Claim, No Drawings

PERFLUOROALKYLACETYL CHLORIDE PROCESS

This application is a division of application Ser. No. 751,013 filed Dec. 16, 1976, now abandoned.

Processes are known for preparing acid chlorides containing perfluoroalkyl groups, using general methods for preparing acyl chlorides, such as they are described in Weygand-Hilgetag, Organisch-chemische Experimentierkunst, 4$^{th}$ edition, 1970, pages 247 through 253. Carboxylic acids are always the starting point, which are put to reaction with an excess of inorganic acid chlorides, e.g. phosphorus trichloride, phosphorus pentachloride, thionyl chloride. Perfluoroalkyl carboxylic acids chlorides are obtained in that way from the corresponding carboxylic acids according to J.Am.-Chem. Soc. 75, 87 (1953) and l.c. 75, 968 (1953). According to British Patent Specification 1,102,903 are prepared in the same manner perfluoroalkylalkylenecarboxylic acid chlorides. A further possibility for preparing acid chlorides containing perfluoroalkyl groups is the reaction of the corresponding carboxylic acids with organic acid chlorides (J. Am. Chem. Soc. 70, 1968 (1948), l.c. 76, 1376 (1954).

All these processes use the analogous carboxylic acid as starting product. The conversion, being quite often incomplete, requires long reaction periods and the work-up of the obtained reaction mixtures is always associated with separating and eliminating by distillation the by-products, which are formed unavoidably, and the starting material which has not participated in the reaction.

Subject of the present invention are perfluoroalkylacetyl chlorides having the general formula

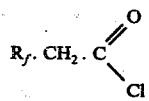   I.

wherein $R_f$ means a straight-chain perfluoroalkyl radical having from 4 to 12, preferably from 6 to 12 carbon atoms.

Subject of the present invention is also a process for preparing such perfluoroalkylacetyl chlorides having general formula

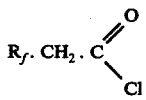   II.

wherein $R_f$ represents a straight-chain or branched perfluoroalkyl radical having 2 to 12 carbon atoms, by reacting perfluoroalkyl ethanols having general formula

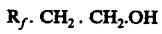   III.

wherein $R_f$ has the same meaning as in formulae I or II, with chlorine-gas while simultaneously exposing to UV irradiation in the presence of an inert organic solvent at temperatures of from $-20°$ C. to $+120°$ C.

The process develops according to the following reaction scheme;

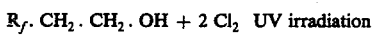

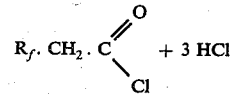

the reaction supposedly running through the step of corresponding aldehydes. The reaction may be carried out discontinuously or continuously as well.

A longitudinally shaped glass cylinder in an upright position, with an UV radiation emitter being located in the center, serves as a most useful reaction vessel for a continuous preparation. The two reactants — chlorine and perfluoroalkyl ethanol dissolved in a solvent — are processed in a counter current; the thoroughly reacted product leaves the glass cylinder through a screen at the lower end and is evacuated through an ascending pipe so as to maintain the level. The chlorine is introduced via a glass frit located immediately above the screen.

2 moles of chlorine are required for one mole of perfluoroalkyl ethanol to be reacted; the chlorine is generally used in a slight excess quantity.

The reaction speed is very high; in general it is proportional to the intensity of the irradiation and, moreover, depends on the size and the shape of the reaction vessel and the installation arrangement of the UV emitter. When a commercially available mercury-low pressure radiator, having a power consumption of about 15 Watt, is used as an irradiation source, from 0.1 to 0.15 mols of a 5 to 10% solution of perfluoroalkyl ethanol per hour can be reacted in an inert solvent in a reaction pipe of about 300 l effective volume. The development and the termination of the reaction can be observed by means of nuclear magnetic resonance spectrum analysis.

The reaction temperature may be chosen randomly within the range of from $-20°$ C. to $+120°$ C., the most useful working range keeps within 0° and 100° C. or at the boiling point of the solvent employed, the reaction heat which is built up and the thermal energy of the UV-irradiation may be removed in that way by a reflux cooling device which is set up sideways.

The thus obtained acid chlorides may be separated from the solvent by distillation. If the obtained product need not satisfy special purity standards, the crude product which is present in the solution may be used directly for further reactions. In that case it is sufficient to eliminate the residual chlorine from the solution by blowing in nitrogen or by subjecting the mixture to a slight distillation.

The alcohols necessary for preparing the acid chlorides of the present invention are commercially available products and, besides, may be manufactured in analogy to German Auslegeschrift 1,214,660, German Offenlegungsschrift 2,318,677 and German Patent Specification 2,028,459. Perfluoroalkyl ethanols in the proper sense of the invention are, for example, perfluorobutyl ethanol, perfluorohexyl ethanol, perfluorooctyl ethanol, perfluorodecyl ethanol, perfluorododecyl ethanol. Mixtures of such alcohols may be successfully used as well.

As solvents in the proper sense of the invention may be understood those being inert against elementary chlorine and UV-irradiation and dissolving at least 1 to 10% of the reactants, such as 1,1,2-trichloro-1,2,2-trifluoroethane, trichlorofluoromethane, tetrachlorodifluoroethane, carbon tetrachloride (halogenated hydrocarbons).

UV-irradiation suitable for carrying out the reaction according to the invention sare the commercially available mercury high pressure or low pressure lamps with an output of about 150 to 15 Watt, made of quartz glass.

The perfluoroalkylacetyl chlorides and their mixtures which have been prepared according to the process of the invention, are valuable intermediate products for the manufacture of e.g. estes by means of reaction with mono- or polyhydric alcohols and of polyglycols and polyglycol ethers, which may be used as surface active substances and textile finishing agents.

Especially the perfluoroalkylacetyl chlorides esterified according to the invention with polyethylene glycols, polypropylene glycols, and with polyglycols having mixed ethylene oxide and propylene oxide units and those obtained by esterification with the corresponding polyglycol monoethers (chain length 2 to 40 alkylene oxide units) are excellent dry cleaning detergents for solid matters, especially for textiles and metal parts in organic solvents. By "dry cleaning detergents" are to be understood surface active substances which enhance and extend the cleaning effect of organic solvents insofar that water can be incorporated into the organic medium and thus the cleaning effect has a grip also on hydrophilic contaminations. These perfluoroalkylacetyl polyether esters have the general formula

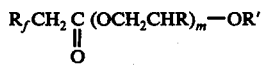

wherein $R_f$ has the aforementioned meaning and wherein $m$ means a number from 2 to 40, R means a hydrogen atom or a methyl group and wherein R' means a hydrogen atom or an alkyl radical with 1 to 4 carbon atoms, mixtures with different values for $m$ or different substituents for R being also included. They are prepared by esterification of the perfluoroalkylacetyl chlorides of the invention with the aforementioned polyglycols or their monoethers according to known methods in the presence of acid-blending agents, e.g. of tertiary amines. The perfluoroalkylacetyl polyether esters of the aforementioned formula may be used as dry cleaning detergents at substantially lower application rates and produce a more important reduction of the interface tension between organic solvent and water than conventional dry cleaning detergents may ever produce.

The process according to the invention for preparing perfluoroalkylacetyl chlorides in comparison to former processes has the undeniable advantage that said chlorides may be obtained by one single processing step — starting from the corresponding alcohols. A further advantage is the fact that the reaction runs practically through to completion, so that high yields are obtained and the resulting products are so pure that they may be reacted further without undergoing any additional purification and elimination of the solvent.

The following examples illustrate the invention

EXAMPLE 1

500 ml of 1,1,2-trichloro-1,2,2-trifluoroethane are filled into a long glass cylinder of about 1 ltr. volume, equipped with a stirrer and a 15-Watt-mercury-low pressure-immersion lamp made of quartz glass being set up in its center. Through a glass frit located at the lower end a constant current of gaseous chlorine, previously dried over concentrated sulfuric acid, is introduced at a speed of about 0.3 l/min, while radiation is going on simultaneously. As soon as the solvent is saturated with gaseous chlorine, 100 g of perfluorooctyl ethanol ($C_8F_{17}.CH_2.CH_2.OH$), dissolved in 500 ml of the same solvent, are added within a period of about 40 minutes and while agitating vigorously. The gaseous hydrogen chloride which is formed as by-product, is removed with some excess chlorine via a reflux cooler set up on top of the reaction vessel and is then neutralized by being introduced into an aqueous sodium hydroxide solution.

After completion of the addition, irradiation and simultaneously metering-in of chlorine is continued for about 5 more minutes at about 26 to 28° C. while agitating, the reaction is then interrupted. The solvent is finally distilled off through a column being replete with glass rings and having a length of 30 cm.

As a residue are obtained 105.8 g (= 99% of the theoretical yield) of a colorless product which is slightly turbid. This product is submitted to another distillation under reduced pressure. 101.8 g (= 95% of the theoretical yield) of perfluorooctylacetyl chloride ($C_8F_{17}.CH_2COCl$) are obtained, having a boiling point of 81 to 82° C. under 11 mm Hg. The colorless, limpid product has a setting point of 29° C.

EXAMPLE 2 through 8:

The perfluoroalkylacetyl chlorides shown in the following table are prepared analogously.

TABLE

| Example | $R_fC_2H_4OH$ | solvent | reaction temperat. | radiator | $R_fCH_2C(=O)Cl$ | kg/mm Hg | melt. point ° C | yield |
|---|---|---|---|---|---|---|---|---|
| 2 | n-$C_2F_5C_2H_4OH$ | $CCl_3F$ | 0° | Hg(Nd) | n-$C_2F_5CH_2C(=O)Cl$ | 79–81°/730 | — | 92% |
| 3 | n-$C_4F_9C_2H_4OH$ | $CCl_4$ | 76° C | Hg(Hd) | $C_4F_9CH_2C(=O)Cl$ | 67°/100 | — | 94% |
| 4 | n-$C_6F_{13}C_2H_4OH$ | $CCl_4$ | 76° C | Hg(Hd) | $C_6F_{13}CH_2C(=O)Cl$ | 60°/12 | — | 96% |

TABLE -continued

| Example | $R_fC_2H_4OH$ | solvent | reaction temperat. | radiator | $R_fCH_2C(=O)Cl$ | kg/mm Hg | melt. point °C | yield |
|---|---|---|---|---|---|---|---|---|
| 5 | n-$C_{10}F_{21}C_2H_4OH$ | 1,1,2-tri- | 47° C | Hg(Hd) | $C_{10}F_{21}CH_2C(=O)Cl$ | 104–105°/11 | 63° | 95% |
| 6 | n-$C_{12}F_{25}C_2H_4OH$ | chloro-1,2,2- | 47° C | Hg(Hd) | $C_{12}F_{25}CH_2C(=O)Cl$ | 119°/11 | 97° | 94% |
| 7 | $(CF_3)_2CF(CF_2)_6C_2H_4OH$ | tri-fluoro-ethane | 47° | Hg(Hd) | $(CF_3)_2CF(CF_2)_6CH_2C(=O)Cl$ | 79°/9 | — | 96% |
| 8 | $CF_3-C(C_2F_5)_2-CH_2CH_2OH$ | | 47° C | Hg(Hd) | $CF_3-C(C_2F_5)_2-CH_2C(=O)Cl$ | 77–77°/100 | — | 93% |

Hg(Nd) : mercury vapor - low-pressure radiator
Hg(Hd) : mercury vapor - high-pressure radiator

EXAMPLE 9

This example describes the continuous preparation of a perfluoroalkylacetyl chloride mixture.

The reaction vessel is a glass cylinder in upright position, having a length of about 25 cm and a diameter of about 5.5 cm and, at the upper end, being equipped with a 15-Watt-immersion lamp, a reflux cooler and a dropping funnel. The empty space around the immersion lamp is replete with Raschig rings above a bottom screen. At the lower end of the reaction vessel a gas inlet pipe is introduced sideways. The product which has undergone the complete reaction, may be evacuated continuously through an ascending pipe which is mounted to rise sideways.

About 350 ml of 1,1,2-trichloro-1,2,2-trifluoroethane are introduced as solvent into the reaction vessel. While simultaneously emitting UV irradiation, a constant current of dry chlorine gas is introduced at a speed of about 100 to 120 ml of chlorine per minute. To this solution of chlorine is added dropwise, at a speed of about 500 ml per hour, a solution of 45.9 g (1/10 mol) of a mixture of perfluoroalkylethanols in 500 ml of the aforementioned solvent, the mixture having the following composition:

| | |
|---|---|
| $C_6F_{13}CH_2CH_2OH$ | 38,6 % |
| $C_8F_{17}CH_2CH_2OH$ | 31,9 % |
| $C_{10}F_{21}CH_2CH_2OH$ | 20,9 % |
| $C_{12}F_{25}CH_2CH_2OH$ | 6,5 % |
| other components | 2,1 % |

(The composition of this industrial alcohol mixture was determined by gas chromatographic analysis).

The thoroughly reacted reaction product is removed from the reaction mixture proportionally to the quantity of fresh product being fed in on the other hand.

The hydrogen chloride being formed during the reaction is passing over at the top of the reflux cooler together with the excess of chlorine; solvent which is distilling off, is condensed by the cooling device fixed on top with a temperature of 0° C. in the cooling tank, and subsequently fed back into the apparatus.

After a total reaction time of 10 hours 459 g of the perfluoroalkyl ethanol-mixture are reacted. When submitting the total reaction solution to a protein resonance spectrum analysis, the result shows that no more starting product is present.

In order to obtain the acid chloride mixture, the solvent and the residual chlorine component are distilled off at 47° C.; the resulting residue is submitted to a distillation in vacuo for purification purposes. These operations yield under a vacuum of 12 mm Hg and at a boiling interval of 58 to 105° C. a quantity of 358.2 g and, after further distillation under a high-vacuum of 0.2 mm Hg and at a boiling interval of 70 to 115° C., a further quantity of 93.5 g of pure acid chloride. When submitting the distillation residue of about 32 g to a proton resonance spectrum analysis, the result shows a presence of 48%, i.e. about 3% of the total yield, of the wanted perfluoroalkylacetyl chlorides in this residue. The total yield of pure acid chloride mixture amounts therefore to about 95%, calculated on the originally used perfluoroalkylethanol mixture. What is claimed is:

1. A process for the manufacture of perfluoroalkylacetyl chlorides having general formula

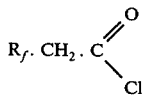
I.

wherein $R_f$ represents a straight-chain or branched perfluoroalkyl radical having from 2 to 12 carbon atoms, which comprises reacting perfluoroalkyl ethanols having general formula

II.

wherein $R_f$ has the same meaning as in formula I, with chlorine under exposure to UV irradiation in the presence of an inert organic solvent, at temperatures of from −20° C. to +120° C.

* * * * *